(12) United States Patent
Mine et al.

(10) Patent No.: US 7,078,559 B2
(45) Date of Patent: Jul. 18, 2006

(54) METHOD OF PRODUCING ACETATE DERIVATIVE

(75) Inventors: Koji Mine, Wakayama (JP); Hisanori Hagi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/889,096

(22) Filed: Jul. 13, 2004

(65) Prior Publication Data

US 2005/0014968 A1 Jan. 20, 2005

(30) Foreign Application Priority Data

Jul. 16, 2003 (JP) ............................. 2003-275307
Jul. 17, 2003 (JP) ............................. 2003-275837

(51) Int. Cl.
*C07C 69/74* (2006.01)

(52) U.S. Cl. ..................................... 560/122

(58) Field of Classification Search ................ 562/509, 562/508, 503, 504; 560/122, 126, 123
See application file for complete search history.

(56) References Cited

U.S. PATENT DOCUMENTS

| 4,163,109 A | * | 7/1979 | Teisseire et al. ............ 560/122 |
| 4,310,701 A | | 1/1982 | Wilson et al. |
| 2004/0171886 A1 | * | 9/2004 | Nishimura et al. ......... 568/343 |

FOREIGN PATENT DOCUMENTS

| EP | 0 033 604 | 8/1981 |
| JP | 53-12842 | 2/1978 |
| JP | 56-147740 | 11/1981 |
| JP | 9-183754 | 7/1997 |

OTHER PUBLICATIONS

Perrard et al, Organic Letters (2000), 2(19), 2959-2962.*

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

The present invention relates to a method of producing an acetate derivative represented by the formula (II) by demonocarboxylating dimalonate represented by the formula (I), wherein water is supplied while the concentration of water in a demonocarboxylating reaction solution is controlled to 0.4% by weight or less to run demonocarboxylation:

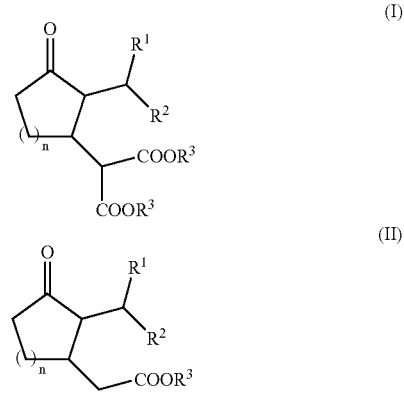

wherein n denotes an integer of 1 or 2, $R^1$ and $R^2$ represent H, a $C_{1-8}$ alkyl group or the like and $R^3$ represents a $C_{1-3}$ alkyl group.

19 Claims, 1 Drawing Sheet

METHOD OF PRODUCING ACETATE DERIVATIVE

FIELD OF THE INVENTION

The present invention relates to a method of producing an acetate derivative useful as raw material for perfumes and physiologically active materials at a high yield and a high selective ratio.

BACKGROUND OF THE INVENTION

There is, for example, a conventional method disclosed in JP-A 53-12842 in which 2-alkyl-3-oxo-cycloalkyl dimalonate is reacted with water having an amount of 1 to 1.5 mol equivalents to the diester at 200 to 260° C. under atmospheric pressure, as a method of producing an acetate derivative by supplying water to a 2-alkyl-3-oxo-cycloalkyl dimalonate to run demonocarboxylation. JP-A 9-183754 discloses a method in which a 2-alkyl-3-oxo-cycloalkyl dimalonate is reacted with water having an amount of 1 to 3 mol equivalents to the diester at 150 to 250° C. JP-A 56-147740 discloses a method in which a 2-alkyl-3-oxo-cycloalkyl dimalonate is reacted with water at 180 to 210° C. under 1 to 10 atmospheric pressures.

SUMMARY OF THE INVENTION

The present invention relates to a method of producing an acetate derivative represented by the formula (II) (hereinafter referred to as "acetate derivative (II)") by demonocarboxylating dimalonate (hereinafter referred to as "dimalonate (I)") represented by the formula (I), wherein water is supplied while the concentration of water in a demonocarboxylating reaction solution is controlled to 0.4% by weight or less to run demonocarboxylation:

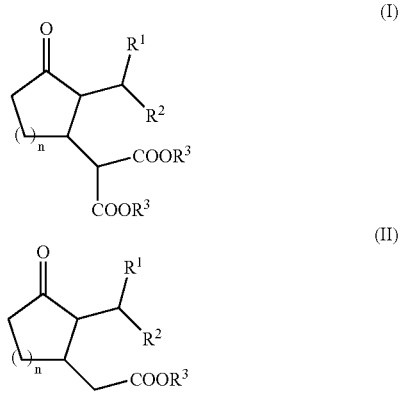

wherein n denotes an integer of 1 or 2, $R^1$ and $R^2$ represent a hydrogen atom or a straight-chain or branched alkyl group having 1 to 8 carbon atoms or may be combined with each other to form a cyclopentane ring or a cyclohexane ring and $R^3$ represents a straight-chain or branched alkyl group having 1 to 3 carbon atoms, provided that the two $R^3$ may be same or different from each other.

The present invention provides another method of producing (II) by supplying water to run demonocarboxylation of (I), in which separating means are prepared outside of the reaction system to run a reaction with removing the generated alcohol and carbon dioxide among the distilled components outside of the system.

DETAILED DESCRIPTION OF THE INVENTION

However, the aforementioned prior art has the following problems. If the reaction temperature is low, the reaction rate is low and therefore, water to be supplied remains excessively in the system and the excess water reacts with the generated acetate derivative, causing a reduction in yield and selective ratio. If the reaction temperature is high, the 2-alkyl-3-oxo-cycloalkyl dimalonate is decomposed, bringing about an inevitable reduction in yield and productivity.

Also, the above prior art has the problem that in these reactions, not only carbon dioxide and alcohol are generated during demonocarboxylation but also unreacted water is vaporized because water is supplied at high temperatures. At this time, a part of the reaction solution is entrained and distilled out of the system, causing an inevitable reduction in yield.

The present invention is to provide a method of producing an acetate derivative from a 2-alkyl-3-oxo-cycloalkyl dimalonate at a high yield and a high selective ratio.

The method of the present invention makes it possible to produce the acetate derivative (II) from the dimalonate (I) at a high yield and a high selective ratio. Because the acetate derivative (II) has small impurities and hence high purity, it can decrease refining load and may be preferably used as raw material for perfumes.

In the dimalonate (I) used as the raw material in the present invention, $R^1$ and $R^2$ show the above meaning. However, as $R^1$ and $R^2$, a hydrogen atom or an alkyl group having 1 to 8 carbon atoms is preferable. It is more preferable that $R^1$ is a hydrogen atom and $R^2$ is an alkyl group having 3 to 5 carbon atoms and it is even more preferable that $R^1$ is a hydrogen atom and $R^2$ is a straight-chain alkyl group having 4 carbon atoms from the viewpoint of using it as the raw material of perfumes. n denotes an integer of 1 or 2, being preferably 1. $R^3$ is a straight-chain or branched alkyl group having 1 to 3 carbon atoms, being preferably a methyl group.

The dimalonate (I) may be produced by a generally known method. For example, a cycloalkanone having 5 or 6 carbon atoms is reacted with an aldehyde represented by the formula (III) or a ketone to obtain a compound represented by the formula (IV). The obtained compound (IV) is subjected to a dehydration reaction and an isomerization reaction to make a compound represented by the formula (V) and the resulting compound is reacted with a compound represented by the formula (VI).

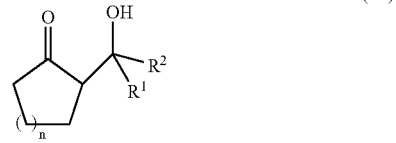

-continued

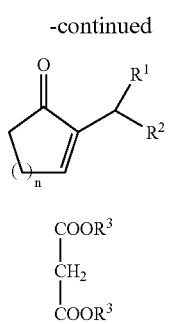

wherein n, $R^1$, $R^2$ and $R^3$ have the same meanings as above.

In the present invention, water is supplied while the concentration of water in the demonocarboxylation reaction solution of the dimalonate (I) is controlled to 0.4% by weight or less and preferably 0.25% by weight or less to run demonocarboxylation.

In this case, the concentration of water is found in the following manner: a sample of the reaction solution is taken and cooled to ambient temperature under a drying circumstance, for example, in a desiccator and then the concentration of water is found by a Karl Fischer's coulometric titration.

Although there is no particular limitation to a method of controlling the concentration of water to 0.4% by weight or less in the reaction solution, the concentration of water is preferably controlled by changing the supply rate of water from the initial stage of the reaction with measuring the concentration of water in the reaction solution such that the concentration of water does not exceed 0.4% by weight. The water to be supplied is preferably steam from the viewpoint of carrying out heating efficiently.

It is desirable to run demonocarboxylation such that the difference (X–Y) between the integrating molar number X (excluding distilled water content) of the water to be supplied and the molar number Y of the water reacted with the dimalonate (I) is kept 20% or less and preferably 15% or less based on the molar number of the dimalonate (I) to be charged since when the conversion ratio of the dimalonate (I) exceeds 50% from the viewpoint of obtaining high yield and high selective ratio.

As to a method of supplying water, it is preferable to supply water from the bottom of a reactor by using a pipe and a sparger, taking the reaction efficiency into account. No particular limitation is imposed on it.

The conversion ratio of the dimalonate (I) in the present invention is found by the following equation from the chromatogram area in gas chromatographic (GC) analysis made under the following condition.

GC Analysis Condition
Column: DB-1 (manufactured by Agilent)
Temperature rise rate: 4° C./min from 80° C. to 200° C.

Conversion ratio (%)={(Area of acetate derivative (II))/(Area of dimalonate (I)+Area of acetate derivative (II))}×100.

The demonocarboxtlation reaction temperature in the present invention is preferably 150° C. or higher, more preferably 170° C. or higher, in consideration of productivity. A wide temperature range from a low temperature to a high temperature may be applicable to the reaction. The reaction temperature is preferably 250° C. or lower, more preferably 230° C. or lower, with the view of preventing the decomposition of the dimalonate (I) and suppressing a reduction in yield. As to the reaction pressure, the reaction is preferably run under normal pressure because no special device is required, though no particular limitation is imposed thereon.

In the present invention, it is preferable to prepare separating means outside of the reaction system when a 2-alkyl-3-cycloalkyl dimalonate is decarboxylated, to run a reaction with removing the generated alcohol and carbon dioxide among the distilled components outside of the system. This suppresses the loss of the reaction solution, making it possible to obtain an acetate derivative in high yield.

In the production method of the present invention, separating means are prepared outside of the reaction system to run a reaction with removing the generated alcohol and carbon dioxide among the distilled components outside of the system when water is supplied to the dimalonate (I) to run demonocarboxylation.

In the present invention, the description reading as follows "separating means are prepared outside of the reaction system" means that separating means such as a separator is prepared outside of the system separately from the reactor used to run the demonocarboxylation reaction.

The separating means in the invention have a mechanism capable of separating the produced alcohol and/or carbon dioxide among the unreacted products, water and reaction products distilled from the reactor.

In the present invention, the produced alcohol and carbon dioxide among the distilled components are removed outside of the system. Components other than these alcohol and carbon dioxide, specifically, components containing the dimalonate (I), the acetate derivative (II) and a compound (hereinafter referred to as "compound (III)) which is produced by the decomposition of the dimalonate (I) during the reaction and represented by the formula (III) are preferably recovered in a reaction vessel.

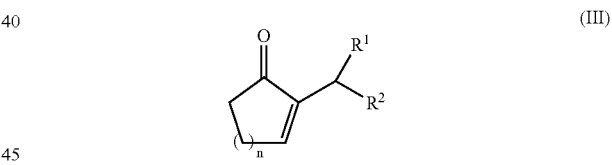

In the formula, n, $R^1$ and $R^2$ have the same meaning as above. Moreover, water is also preferably recovered in the reactor vessel from the viewpoint of using the supplied water efficiently.

Examples of the means for separating the distilled components include directly separating means and means provided with a cooler installed to condense vapor thereby separating the vapor or the like. Examples of the means of separating vapor directly include means such as membrane separation, adsorption and absorption. Also, examples of the means separating by condensing vapor include rectification and partial condensation. The means of separating by condensing vapor are preferable in consideration of separation efficiency and recovery efficiency.

In the case of separating the distilled components by rectification, a rectifier is preferably installed on the top of reaction vessel to carry out refluxing thereby returning a component containing one or more types of the dimalonate (I), acetate derivative (II), compound (III) and water to the reaction vessel and the produced alcohol is condensed in, for example, a condenser or the like installed outside of the system and is removed selectively outside of the system with carbon dioxide.

In the case of separating the distilled components by partial condensation, two or more cooling tubes (condensers) are installed in series to provide a difference between the temperatures of the cooling media and to control the flow rate of the cooling media, which enables selective separation of a component containing at least one or more types of the dimalonate (I), acetate derivative (II), compound (III) and water from alcohol and carbon dioxide. Although the component containing at least one of the dimalonate (I), acetate derivative (II), compound (III) and water may be returned to the reaction vessel after the reaction is finished or used in the next reaction, they are preferably returned continuously to the reaction vessel to run an effective reaction.

In the case of producing industrially, it is preferable to control the vapor temperature of the top of the rectifier in the case of rectification and to control the outlet temperature of the vapor side of the cooling tube in the case of partial condensation to separate the component containing at least one of the dimalonate (I) acetate derivative (II), compound (III) and water efficiently from alcohol and carbon dioxide. The generated carbon dioxide may be recovered by an absorbing operation.

Figure 1:
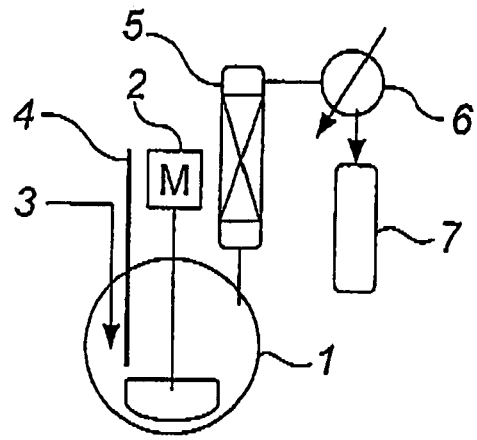
FIG. 1 is a schematic view of a reactor used in Example 3.

The symbols in the drawings are as follows:
1. Reaction vessel (Reactor)
2. Stirrer
3. Supply unit
4. Thermometer
5. Packed column
6. Cooling tube (condenser)
7. Receiver
8. Cooling tube (condenser)
9. Cooling tube (condenser)
10. Reaction vessel (Reactor)
11. Rectifier
12. Cooling tube (condenser)
13. Reaction vessel (Reactor)
14. Thermometer
15. Thermometer

EXAMPLES

The raw materials and the products (reaction product) obtained after the reaction was finished were analyzed by a gas chromatography internal standard method (column: DB-1 (manufactured by Agilent), temperature rise rate: 4° C./min from 80° C. to 200° C.).

Production Example 1

A 6 m$^3$ reaction vessel equipped with a dropping vessel was charged with 2241 kg (26.6 kmol) of cyclopentanone, 1007 kg of water and 11 kg of 48% NaOH and these components were cooled to 15° C. with stirring. Then, 985 kg (11.4 kmol) of valeraldehyde was dropped to the mixture at the same temperature over 5 hours. After drop was finished, the mixture was stirred at the same temperature for one hour. After the reaction was finished, the reaction solution was neutralized. Unreacted cyclopentanone was recovered by distillation and then the organic phase was analyzed. As a result, it was found that 1706 kg of 2-(1-hydroxypentyl)cyclopentanone was included in 1868 kg of the reaction product.

0.0206 mol of oxalic acid was added to the above reaction product containing 1.01 mol of 2-(1-hydroxypentyl)cyclopentanone and the mixture was reacted at 120° C. The amount of 2-pentylidenecyclopentanone contained in the reaction product was 141 g (0.93 mol). A product obtained by filtering the reaction product was dissolved in 153 g of n-butanol, which was then raised to 130° C. Then, a mixed solution of 14.5 g (0.15 mol) of 3-picoline and 10.5 g (0.1 mol) of 35% hydrochloric acid was dropped to the above product at the same temperature for 30 minutes. After drop was finished, the mixture was stirred under heating at the same temperature for 3.5 hours. After the reaction was finished, the reaction mixture was cooled to ambient temperature and neutralized by adding an aqueous sodium hydroxide solution. Then, the organic phase was analyzed and as a result, it was found that 118 g of 2-pentyl-2-cyclopentenone was contained in the reaction product.

The reaction product was refined to obtain 95 g (0.6 mol) of 2-pentyl-2-cyclopentenone. Moreover, 95 g (0.6 mol) of 2-pentyl-2-cyclopentenone was dropped to a solution, prepared by dissolving 118 g (0.9 mol) of dimethyl malonate in 38 g of methanol anhydride in a nitrogen atmosphere, cooling the mixture to 0° C. and adding 6.5 g (0.036 mol) of sodium methoxide (30% methanol solution), at 0° C. over 2 hours. After the addition was finished, unreacted dimethyl malonate was vacuum-distilled to obtain 160 g of dimethyl 2-pentyl-3-oxo-cyclopentylmalonate.

Example 1

A 1 L four-neck flask equipped with a stirrer, a supply unit, a thermometer and a rectifier was charged with 600 g of raw material containing 545 g (1.92 mol) of dimethyl 2-pentyl-3-oxo-cyclopentylmalonate produced in the same manner as in Production Example 1 and the raw material was heated to 180° C. with stirring under normal pressure. Then, the supply of water to the bottom of the reactor was started. During the supply of water, the supply rate of water was adjusted to 6 g/h from the start of the supply to the 2nd hour, to 3 g/h from the 2nd hour to the 8th hour and to 1.2 g/h after the 8th hour with measuring the content of water in the reaction solution by a Karl Fischer's coulometric titration (instrument: Trace-water measuring device AQ-7, manufactured by HIRANUMA SANGYO Co., Ltd.) such that the content of water was limited to 0.4% by weight or less. Then, the reaction was completed for 16 hours from the start of the supply of water. The maximum water concentration in the reaction solution was 0.21% by weight. During the reaction, the difference (X–Y) between the integrating molar number X (excluding distilled water content) of the water to be supplied and the molar number Y of the water reacted with dimethyl 2-pentyl-3-oxo-cyclopentylmalonate was 14.8% at a maximum based on the molar number of the charged dimethyl 2-pentyl-3-oxo-cyclopentylmalonate. It was found that the reaction product contained 423 g (1.87 mol, yield: 97.3%) of methyl 2-pentyl-3-oxo-cyclopentylacetate and 10.8 g (0.051 mol) of 2-pentyl-3-oxo-cyclopentylacetic acid.

Comparative Example 1

The same 1 L four-neck flask that was used in Example 1 was charged with 600 g of raw material containing 557 g (1.96 mol) of dimethyl 2-pentyl-3-oxo-cyclopentylmalonate produced in the same manner as in Production Example 1 and the raw material was heated to 180° C. with stirring under normal pressure. Then, the supply of water to the bottom of the reactor was started. During the supply of water, the supply rate of water was adjusted to a constant rate (6 g/h). Then, the reaction was completed for 9 hours from the start of the supply of water. During the supply of water, the content of water in the reaction solution was measured by a Karl Fischer's coulometric titration (instrument: Trace-water measuring device AQ-7, manufactured by HIRANUMA SANGYO Co., Ltd.) and as a result, the maximum water concentration in the reaction solution was 0.44% by weight. It was found that the reaction product contained 402 g (1.78 mol, yield: 90.7%) of methyl 2-pentyl-3-oxo-cyclopentylacetate and 33.5 g (0.158 mol) of 2-pentyl-3-oxo-cyclopentylacetic acid.

Example 2

The same 1 L four-neck flask that was used in Example 1 was charged with 600 g of raw material containing 550 g (1.94 mol) of dimethyl 2-pentyl-3-oxo-cyclopentylmalonate produced in the same manner as in Production Example 1 and the raw material was heated to 215° C. with stirring under normal pressure. Then, the supply of water to the bottom of the reactor was started. During the supply of water, the supply rate of water was adjusted to 18 g/h from the start of the supply to the 1st hour, to 12 g/h from the 1st hour to the 2nd hour, to 6 g/h from the 2nd hour to the 3rd hour and to 3 g/h after the 3rd hour with measuring the content of water in the reaction solution by a Karl Fischer's coulometric titration (instrument: Trace-water measuring device AQ-7, manufactured by HIRANUMA SANGYO Co., Ltd.) such that the content of water was limited to 0.4% by weight or less. Then, the reaction was completed for 4 hours from the start of the supply of water. The maximum water concentration in the reaction solution was 0.14% by weight. During the reaction, the difference (X−Y) between the integrating molar number X (excluding distilled water content) of the water to be supplied and the molar number Y of the water reacted with dimethyl 2-pentyl-3-oxo-cyclopentylmalonate was 10.3% at a maximum based on the molar number of the supplied dimethyl 2-pentyl-3-oxo-cyclopentylmalonate. It was found that the reaction product contained 420 g (1.86 mol, yield: 96.0%) of methyl 2-pentyl-3-oxo-cyclopentylacetate and 5.8 g (0.027 mol) of 2-pentyl-3-oxo-cyclopentylacetic acid.

The reaction condition and the results in Examples 1 and 2 and Comparative Example 1 are collectively shown in Table 1.

TABLE 1

| | Temperature [° C.] | Material Pressure | Dimalonate (I)*1 [g] | [g] | [mol] | Water supply rate | Maximum water concentration in the reaction solution [% by weight] | Z*4 [%] | Reaction time [h] | Acetate derivative (II)*2 Yield [g] [mol] [%] | Acetic acid derivative*3 Yield [g] [mol] [%] |
|---|---|---|---|---|---|---|---|---|---|---|---|
| Example 1 | 180 | Normal pressure | 600 | 545 | 1.92 | 0~2 h: 6 g/h 2~8 h: 3 g/h 8~16 h: 1.2 g/h | 0.21 | 14.8 | 16 | 423  1.87  97.3 | 10.8  0.051  2.7 |
| Example 2 | 215 | Normal pressure | 600 | 550 | 1.94 | 0~1 h: 18 g/h 1~2 h: 12 g/h 2~3 h: 6 g/h 3~4 h: 3 g/h | 0.14 | 10.3 | 4 | 420  1.86  96.0 | 5.8  0.027  1.4 |
| Comparative example 1 | 180 | Normal pressure | 600 | 557 | 1.96 | 6 g/h | 0.44 | — | 9 | 402  1.78  90.7 | 33.5  0.158  8.0 |

*1Dimethyl 2-pentyl-3-oxo-cyclopentylmalonate
*2Methyl 2-pentyl-3-oxo-cyclopentylacetate
*3 2-pentyl-3-oxo-cyclopentylacetic acid
*4Maximum value of (X−Y) based on the molar number of the dimalonate (I) to be charged.

Example 3

A reactor shown in FIG. 1 which was provided with a reaction vessel 1 constituted of a 1 L four-neck flask equipped with a stirrer 2, a supply unit 3, a thermometer 4 and a Packed column 5 and a cooling tube (condenser) 6 and a receiver 7 installed downstream of the Packed column 5 was used to run a reaction.

The reaction vessel 1 was charged with 600 g of raw material containing 556 g (1.96 mol) of dimethyl 2-pentyl-3-oxo-cyclopentylmalonate produced in the same manner as in Production Example 1 and the raw material was heated to 215° C. with stirring under normal pressure. Then, water was supplied from the supply unit 3 at a rate of 12 g/h. Among the vapor generated during the reaction, components containing methyl 2-pentyl-3-oxo-cyclopentylacetate, dimethyl 2-pentyl-3-oxo-cyclopentylmalonate and 2-pentyl-2-cyclopentenone and water were condensed in the Packed column 5 and returned continuously to the reaction vessel 1. Methanol was distilled out of the system, condensed in the condenser 6 and recovered in the receiver 7. Then, the reaction was completed for 3.75 hours from the start of the supply of water. It was found that the reaction product contained 413 g (1.83 mol, yield: 93.5%) of methyl 2-pentyl-3-oxo-cyclopentylacetate and 69.8 g (2.18 mol) of methanol could be recovered from the fractions condensed outside of the system.

Example 4

Figure 2:
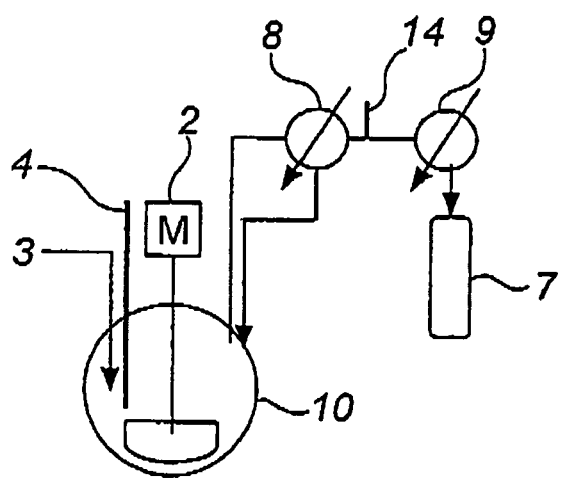
FIG. 2 is a schematic view of a reactor used in Example 4.

A reactor shown in FIG. 2 which was provided with a reaction vessel 10 constituted of a 2 L four-neck flask equipped with a stirrer 2, a supply unit 3 and a thermometer 4, a cooler provided with two cooling tubes (condensers) 8 and 9 arranged in series and a thermometer 14 arranged between the two cooling tubes and a receiver 7 was used to run a reaction.

The reaction vessel 10 was charged with 1111 g of raw material containing 1068 g (3.76 mol) of dimethyl 2-pentyl-3-oxo-cyclopentylmalonate produced in the same manner as in Production Example 1 and the raw material was heated to 180° C. with stirring under normal pressure. Then, the supply of water from supply unit 3 was started. During the supply of water, the supply rate of water was adjusted to 11.6 g/h from the start of the supply to the 2nd hour, to 5.6 g/h from the 2nd hour to the 8th hour and to 2.3 g/h after the 8th hour. Among the vapor generated during the reaction, components containing methyl 2-pentyl-3-oxo-cyclopentylacetate, dimethyl 2-pentyl-3-oxo-cyclopentylmalonate and 2-pentyl-2-cyclopentenone and water were condensed in the first cooling tube 8 with controlling the supply rate of cooling water such that the vapor temperature was 65° C. at the outlet of the cooling tube 8 and returned continuously to the reaction vessel 10, and methanol was condensed in the second cooling tube 9 with supplying a 0° C. cooling medium and recovered in the receiver 7. Then, the reaction was completed for 15 hours from the start of the supply of water. The reaction product contained 811 g (3.59 mol, yield: 95.5%) of methyl 2-pentyl-3-oxo-cyclopentylacetate and 132.6 g (4.14 mol) of methanol could be recovered from the fraction condensed outside of the system.

Example 5

Figure 3:
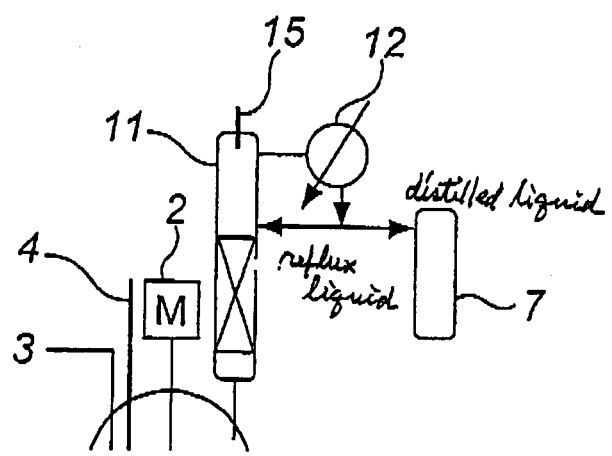
FIG. 3 is a schematic view of a reactor used in Example 5.

A reactor shown in FIG. 3 which was provided with a reaction vessel 13 constituted of a 3 L four-neck flask equipped with a stirrer 2, a supply unit 3, a thermometer 4 and a rectifier 11 with 15-stages, a cooling tube (condenser) 12 and a receiver 7 which were installed downstream of the rectifier 11 provided with a thermometer 15 was used to run a reaction.

The reaction vessel 13 was charged with 1933 g of raw material containing 1840 g (6.48 mol) of dimethyl 2-pentyl-3-oxo-cyclopentylmalonate produced in the same manner as in Production Example 1 and the raw material was heated to 180° C. with stirring under normal pressure. Then, the supply of water from supply unit 3 was started. During the supply of water, the supply rate of water was adjusted to 19 g/h from the start of the supply to the 2nd hour, to 9.5 g/h from the 2nd hour to the 8th hour and to 3.8 g/h after the 8th hour. Among the vapor generated during the reaction, components containing methyl 2-pentyl-3-oxo-cyclopentylacetate, dimethyl 2-pentyl-3-oxo-cyclopentylmalonate and 2-pentyl-2-cyclopentenone and water were refluxed continuously to the reaction vessel 13 at a reflux ratio of 5, while maintaining the top temperature of the rectifier at 65° C. Methanol was condensed in the condenser 12 outside of the system and recovered in the receiver 7. Then, the reaction was completed for 14 hours from the start of the supply of water. The reaction product contained 1414 g (6.26 mol, yield: 96.6%) of methyl 2-pentyl-3-oxo-cyclopentylacetate and 177.2 g (5.54 mol) of methanol could be recovered from the fraction condensed outside of the system.

The reaction condition and results of Examples 3 to 5 are shown collectively in Table 2.

TABLE 2

| | Temperature [° C.] | Pressure | Raw material [g] | Dimalonate (I)*1 [g] | [mol] | Water supply flow rate | Separating means | Reaction time [h] | Acetate derivative(II) in the reaction vessel*2 [g] | [mol] | Yield [%] | Methanol in the receiver [g] | [mol] |
|---|---|---|---|---|---|---|---|---|---|---|---|---|---|
| Example 3 | 215 | Normal pressure | 600 | 556 | 1.96 | 12 g/h | Packed column Cooling tube | 3.75 | 413 | 1.83 | 93.5 | 69.8 | 2.18 |
| Example 4 | 180 | Normal pressure | 1111 | 1068 | 3.76 | 0~2 h: 11.6 g/h 2~8 h: 5.6 g/h 8~15 h: 2.3 g/h | Partial condensation | 15 | 811 | 3.59 | 95.5 | 132.6 | 4.14 |
| Example 5 | 180 | Normal pressure | 1933 | 1840 | 6.48 | 0~2 h: 19 g/h 2~8 h: 9.5 g/h 8~14 h: 3.8 g/h | Rectification | 14 | 1414 | 6.26 | 96.6 | 177.2 | 5.54 |

*1Dimethyl 2-pentyl-3-oxo-cyclopentylmalonate
*2Methyl 2-pentyl-3-oxo-cyclopentylacetate

What is claimed is:

1. A method of producing an acetate derivative represented by formula (II), comprising demonocarboxylating a dimalonate represented by formula (I) by reacting the dimalonate represented by formula (I) with water to obtain the acetate derivative (II), wherein said water is supplied to a reaction vessel for said demonocarboxylating while the concentration of water in a demonocarboxylating reaction solution in a said reaction vessel is controlled to 0.4% by weight or less:

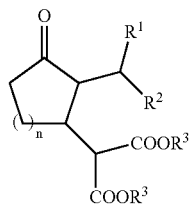

(I)

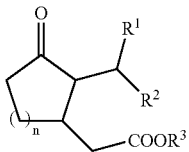

(II)

wherein n denotes an integer of 1 or 2, $R^1$ and $R^2$ represent a hydrogen atom or a straight-chain or branched alkyl group having 1 to 8 carbon atoms or may be combined with each other to form a cyclopentane ring or a cyclohexane ring and $R^3$ represents a straight-chain or branched alkyl group having 1 to 3 carbon atoms, provided that the two $R^3$s may be same or different from each other, and wherein said demonocarboxtlating is at a reaction temperature of at least 150° C.

2. The method according to claim 1, wherein the difference (X−Y) is 20% or less based on the molar number of the dimalonate represented by formula (I) to be charged,
wherein X is the integrating molar number of water to be supplied to said reaction vessel, excluding distilled water content, and
wherein Y is the molar number of water to reacted with the dimalonate represented by formula (I).

3. The method according to claim 1, wherein said water is supplied at a variable supply rate.

4. The method according to claim 1, wherein said demonocarboxylating is a distillation process in which separating means are disposed outside of the system to remove alcohol and carbon dioxide from distilled components formed during said distillation.

5. The method according to claim 4, wherein the distilled components comprise at least one dimalonate represented by formula (I), the acetate derivative represented by formula (II), a decomposition product of the dimalonate represented by formula (I) and water are separated by condensation,
wherein said decomposition product of the dimalonate represented by formula (I) is a compound represented by formula (III):

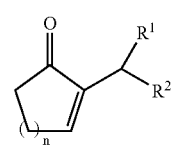

(III)

wherein n denotes an integer of 1 or 2, $R^1$ and $R^2$ represent a hydrogen atom or a straight-chain or branched alkyl group having 1 to 8 carbon atoms or may be combined with each other to form a cyclopentane ring or a cyclohexane ring.

6. The method according to claim 4, wherein the distilled components comprise at least one dimalonate represented by formula (I), the acetate derivative represented by formula (II), a decomposition product of the dimalonate represented by formula (I) and water are separated from alcohol and carbon dioxide produced by said demonocarboxylating by rectifying,
wherein said decomposition product of the dimalonate represented by formula (I) is a compound represented by formula (III):

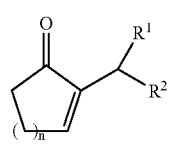

(III)

wherein n denotes an integer of 1 or 2, $R^1$ and $R^2$ represent a hydrogen atom or a straight-chain or branched alkyl group having 1 to 8 carbon atoms or may be combined with each other to form a cyclopentane ring or a cyclohexane ring.

7. The method according to claim 4, wherein the distilled components comprise at least one dimalonate represented by formula (I), the acetate derivative represented by formula (II), a decomposition product of the dimalonate represented by formula (I) and water are separated from alcohol and carbon dioxide produced by said demonocarboxylating by partial condensation,
wherein said decomposition product of the dimalonate represented by formula (I) is a compound represented by formula (III):

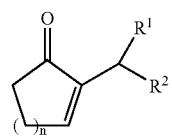

(III)

wherein n denotes an integer of 1 or 2, $R^1$ and $R^2$ represent a hydrogen atom or a straight-chain or branched alkyl group having 1 to 8 carbon atoms or may be combined with each other to form a cyclopentane ring or a cyclohexane ring.

8. The method according to claim 4, wherein at least one dimalonate represented by formula (I), the acetate derivative represented by formula (II) and water are returned continuously to said reaction vessel.

9. The method according to claim 1, wherein said water is supplied in the form of steam.

10. The method according to claim 1, wherein said water is supplied from the bottom of said reaction vessel a pipe and a sparger.

11. The method according to claim 1, wherein said demonocarboxylating is at a reaction temperature of at least 170° C.

12. The method according to claim 1, wherein said demonocarboxylating is conducted at ambient pressure.

13. The method according to claim 4, wherein said separating means is selected from the group consisting of a directly separating means and a means provided with a cooler installed to condense vapor.

14. The method according to claim 13, wherein said separating means is a directly separating means, which is selected from the group consisting of a membrane separation, adsorption and absorption.

15. The method according to claim 13, wherein said separating means is a means provided with a cooler installed to condense vapor, which is selected from the group consisting of rectification and partial condensation.

16. The method according to claim 5, wherein said at least one dimalonate represented by formula (I), said acetate derivative represented by formula (II), and said compound represented by formula (III), and water are returned continuously to said reaction vessel.

17. The method according to claim 6, wherein said at least one dimalonate represented by formula (I), said acetate derivative represented by formula (II), and said compound represented by formula (III), and water are returned continuously to said reaction vessel.

18. The method according to claim 7, wherein said at least one dimalonate represented by formula (I), said acetate derivative represented by formula (II), and said compound represented by formula (III), and water are returned continuously to said reaction vessel.

19. The method according to claim 1, wherein the difference (X−Y) is 15% or less based on the molar number of the dimalonate represented by formula (I) to be charged.

* * * * *